United States Patent [19]

Dürr et al.

[11] Patent Number: 4,495,350
[45] Date of Patent: Jan. 22, 1985

[54] HETEROCYCLIC ESTERS OF 2-NITRO-5-(O-CHLORO-P-TRIFLUOROMETHYLPHENOXY)-BENZOIC ACID

[75] Inventors: Dieter Dürr, Bottmingen; Otto Rohr, Therwil; Beat Böhner, Binningen, all of Switzerland

[73] Assignee: Ciba Geigy Corporation, Ardsley, N.Y.

[21] Appl. No.: 417,744

[22] Filed: Sep. 13, 1982

Related U.S. Application Data

[62] Division of Ser. No. 107,983, Dec. 28, 1979, Pat. No. 4,455,437.

[30] Foreign Application Priority Data

Jan. 9, 1979 [CH] Switzerland ............... 168/79

[51] Int. Cl.³ ............... C07D 295/14; C07D 213/55
[52] U.S. Cl. .................. 544/167; 544/58.1; 544/394; 544/399; 546/235; 546/335; 548/541; 548/569; 260/239 BE
[58] Field of Search ............ 544/58.1, 167, 394, 544/399; 546/235, 335; 548/541, 569; 260/239 BE

[56] References Cited

U.S. PATENT DOCUMENTS 4,093,446 6/1978 Bayer et al. .................. 544/167
4,146,385 3/1979 Majoie ........................ 71/116

*Primary Examiner*—Robert W. Ramsuer
*Attorney, Agent, or Firm*—Frederick H. Rabin

[57] ABSTRACT

Herbicidally effective aminoalkyl esters of 2-nitro-5-(o-chloro-p-trifluoromethylphenoxy)-benzoic acid, and acid addition salts and quaternary ammonium salts thereof, are suitable for the selective control of weeds in crops of useful plants, for example soya bean and rice crops.

The aminoalkyl esters correspond to the formula

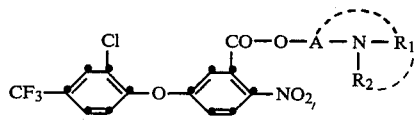

wherein A is a $C_2$–$C_4$-alkylene bridge or the direct bond, and

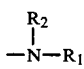

is an open amino group, and

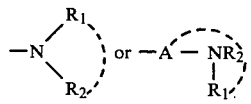

is a cyclic amino group.

9 Claims, No Drawings

HETEROCYCLIC ESTERS OF 2-NITRO-5-(O-CHLORO-P-TRIFLUOROMETHYL-PHENOXY)-BENZOIC ACID

This is a division of application Ser. No. 107,983 filed on Dec. 28, 1979 now U.S. Pat. No. 4,455,437.

The present invention relates to novel aminoalkyl esters of 2-nitro-5-(o-chloro-p-trifluoromethylphenoxy)benzoic acid having a herbicidal action, and acid addition and quaternary salts thereof, to processes for producing them, to compositions containing them as active substance, and to their use as selective herbicides.

The aminoalkyl esters of 2-nitro-5-(o-chloro-p-trifluoromethylphenoxy)-benzoic acid correspond to the formula I

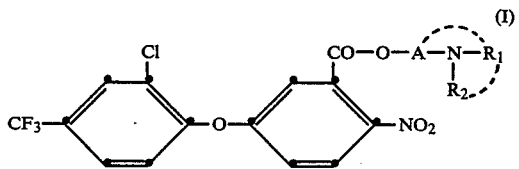

wherein
A is a branched-chain or straight-chain $C_2$–$C_4$-alkylene group or the direct bond,
$R_1$ is $C_1$–$C_4$-alkyl which is unsubstituted or substituted by halogen, cyano or hydroxyl, or is interrupted by oxygen or sulfur, or it is $C_3$–$C_5$-alkenyl or alkynyl both unsubstituted or substituted by halogen,
$R_2$ is a bond, hydrogen or has the same meaning as $R_1$,
$R_1$ and $R_2$ or $R_1$ and a carbon atom of A together with the nitrogen atom to which they are bound likewise form a 5–7-membered heterocycle which can be interrupted by oxygen, sulfur or $>NR_3$, and
$R_3$ is hydrogen, $C_1$–$C_4$-alkyl, phenyl or benzyl.

Suitable as active substances are also the acid addition salts and quaternary ammonium salts of these aminoalkyl esters, which salts correspond to the formula Ia

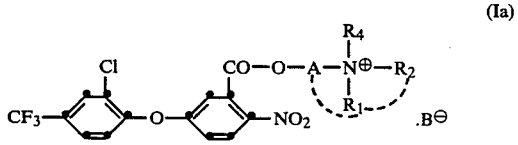

wherein A, $R_1$ and $R_2$ have the meanings defined above, $R_4$ is $C_1$–$C_6$-alkyl which is unsubstituted or substituted by hydroxyl or methoxy, or it is benzyl, and B is the anion of an organic or inorganic acid.

The alkylene groups A in this formula embrace the ethylene, propylene and butylene groups, such as the branched-chain groups 1-methylethylene, 2-methylethylene, 1-methylpropylene, 2-methylpropylene and 3-methylpropylene, as well as 1,2-dimethylethylene.

The alkyl groups $R_1$, $R_2$, $R_3$ and $R_4$ can be straight-chain or branched-chain, and likewise the alkenyl and alkynyl groups $R_1$ and $R_2$. Possible substituents of the groups $R_1$ and $R_2$ are halogen atoms, particularly chlorine, bromine and iodine; they can moreover be substituted by cyano or hydroxyl, or be interrupted by oxygen or sulfer.

Suitable heterocycles are in particular pyrrolidine, pyridine, piperidine, azepine, morpholine, piperazine and thiomorpholine. These rings can be mono- or disubstituted by $C_1$–$C_4$-alkyl groups or halogen atoms, or they can also be interrupted by a carbonyl group.

Suitable acids for forming salts are the hydrogen halides, sulfuric acid, organic sulfuric acids, phosphoric acid or organic acids, for example fatty acids. Suitable for quaternisation are in particular alkyl or benzyl halides, as well as alkyl or benzyl esters of toluenesulfonic acid.

2-Nitro-5-(o-chloro-p-trifluoromethylphenoxy)-benzoic acid is known from the U.S. Pat. No. 3,928,416. It has a herbicidal action but is fairly phytotoxic. The aminoalkyl esters and acid addition salts thereof according to the invention surprisingly exhibit, whilst having an equally good herbicidal action, valuable selectivity with respect to dicotyledonous cultivated plants, especially soya bean plants.

From U.S. Pat. No. 3,784,635 are also known 2-nitro-5-tolueneoxy-benzoic acid esters and amides having a herbicidal action.

The aminoalkyl esters of 2-nitro-5-(o-chloro-p-trifluoromethylphenoxy)-benzoic acid of the formula I and acid addition salts thereof are produced in a manner known per se.

One process comprises reacting a halide of 2-nitro-5-(o-chloro-p-trifluoromethylphenoxy)-benzoic acid of the formula II

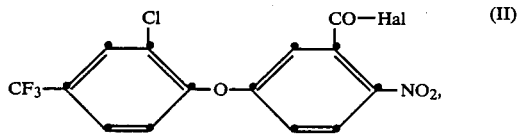

wherein "Hal" is chlorine or bromine, with the aminoalkanol of the formula III

wherein A, $R_1$ and $R_2$ have the meanings defined under the formula I.

The reaction is performed advantageously in a solvent inert to the reactants, optionally in the presence of the molar amount of an acid-binding agent, depending on whether it is desired to obtain as the final product the aminoalkyl ester or an acid addition salt thereof. The temperature of this reaction can vary between room temperature and the boiling point of the reaction mixture.

Some compounds can be produced by firstly reacting the benzoic acid halide of the formula II with a halogenoalkanol of the formula IV

wherein A has the meaning defined under the formula I, and "Hal" is chlorine or bromine, to give the halogenoalkyl ester of 2-nitro-5-(o-chloro-p-trifluoromethylphenoxy)-benzoic acid of the formula V

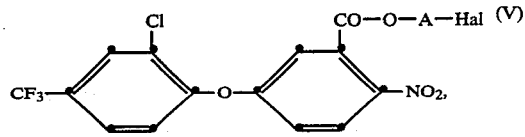

wherein A and "Hal" have the meanings given above, and then reacting this product with an amine of the formula VI

wherein R₁ and R₂ have the meanings defined under the formula I, optionally in the presence of the equimolar amount of an acid-binding agent. This process too is advantageously performed in a solvent inert to the reactants, at a temperature between room temperature and the boiling point of the reaction mixture.

Where they do not already occur in salt form from the reaction, acid addition salts of aminoalkyl esters of the formula I can be obtained in a simple manner by bringing together equimolar amounts of the amino ester and of the acid in an inert solvent.

Conversely, it is possible to obtain from an acid addition salt of the free amino ester, by the addition of a small excess of a base, best of all of a tertiary amine, in an aqueous solution in the presence of an inert solvent immiscible with water. The ester passes into the solvent phase and can be obtained by evaporating off the solvent.

The quaternary ammonium salts can likewise be obtained by bringing together equimolar amounts of the amino ester of the formula I with an ester of the formula VI $$R_4-B \qquad (VI)$$

wherein B and R₄ have the defined meaning, in an inert solvent; the salts can subsequently be isolated by evaporating off the solvent.

The production of 2-nitro-5-(o-chloro-p-trifluoromethylphenoxy)-benzoic acid is known, and is described in the U.S. Pat. No. 3,928,416.

The method of producing the aminoalkyl esters of the invention can be seen from the following Examples. The temperatures are given in degrees Centigrade, and percentage values and parts relate to weight. Following the Examples, there are listed in a Table further compounds produced in an analogous manner.

The aminoalkyl esters have negligible toxicity for humans and animals, and the handling of them requires no special precautionary measures. They are soluble in the customary solvents, such as hydrocarbons, ethers, ketones and chlorinated hydrocarbons.

EXAMPLE 1

2-Nitro-5-(o-chloro-p-trifluoromethylphenoxy)-benzoic acid-2″-dimethylaminoethyl ester

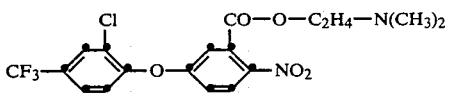

18.5 g of 2-nitro-5-(o-chloro-p-trifluoromethylphenoxy)-benzoic acid in 100 ml of toluene, with 10 ml of thionyl chloride and a drop of dimethylformamide, is heated at 80° for two hours; the solvent is then distilled off in vacuo, and the residue is taken up in 50 ml of toluene. This solution of 2-nitro-5-(o-chloro-p-trifluoromethylphenoxy)-benzoyl chloride is added dropwise at 20°–60°, with stirring, to a solution of 20 g of 2-dimethylaminoethanol and 28 ml of triethylamine in 200 ml of toluene. After one hour, the reaction mixture is poured into water. The organic layer is washed with water, dried, and concentrated by evaporation to obtain, in practically quantitative yield, the above-given ester in the form of oil, which solidifies after trituration with hexane, m.p. 73°–75°.

EXAMPLE 2

2-Nitro-5-(o-chloro-p-trifluoromethylphenoxy)-benzoic acid-2″-methylamino-ethyl ester (hydrochloride)

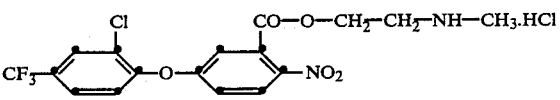

20 g of 2-nitro-5-(o-chloro-p-trifluoromethylphenoxy)-benzoic acid-2″-bromoethyl ester with 2.8 g of methylamine is allowed to stand in 300 ml of ether. The course of the reaction is followed by means of thin-layer chromatography. Further processing consists of stirring the reaction mixture up with a diluted sodium carbonate solution, separating the ether layer, and drying it over sodium sulfate. The ether solution is filtered, and subsequent concentration by evaporation yields the free base of the title compound in the form of highly viscous oil. The hydrochloride is prepared by passing anhydrous hydrochloric acid gas into the ether solution; m.p. 105°.

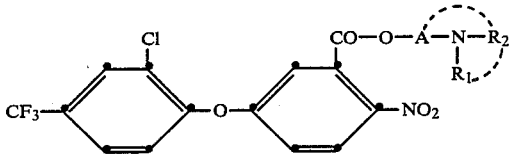

| No. | $A-N\begin{smallmatrix}R_1\\R_2\end{smallmatrix}$ | Physical constants |
|---|---|---|
| 1 | —C₂H₄N(CH₃)₂ | m.p. 73–75° |
| 2 | —C₃H₆N(CH₃)₂ | $n_D^{23.5}$ 1.5314 |
| 3 | CH(CH₃)CH₂N(CH₃)₂ | $n_D^{24.5}$ 1.5285 |
| 4 | CH(CH₃)CH₂N⟨ ⟩O | $n_D^{22}$ 1.5296 |
| 5 | —C₂H₄N(C₂H₅)₂ | $n_D^{24}$ 1.5350 |
| 6 | CH₂CH(CH₃)N(CH₃)₂ | $n_D^{24}$ 1.5394 |

-continued

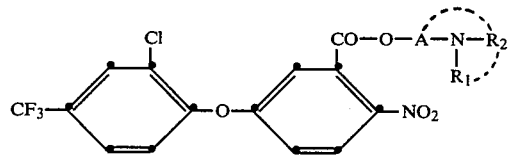

| No. | $\begin{smallmatrix}A-N-R_1\\|\\R_2\end{smallmatrix}$ | Physical constants |
|---|---|---|
| 7 | 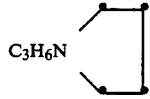 C₃H₆N | $n_D^{24}$ 1.5394 |
| 8 | 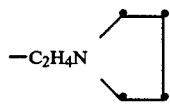 —C₂H₄N | $n_D^{23}$ 1.5455 |
| 9 | 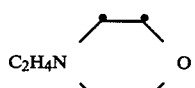 C₂H₄N  O | $n_D^{25}$ 1.5455 |
| 10 | 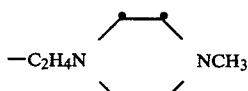 —C₂H₄N  NCH₃ | |
| 11 | —C₂H₄N(CH₂CH=CH₂)₂ | |
| 12 | —C₂H₄N(CH₂C≡CH)₂ | |
| 13 | —C₂H₄N(C₂H₄OH)₂ | |
| 14 | C₂H₄N—CH—C≡CH | |
| 15 | —C₂H₄N(CH₃)N—C₂H₄OCH₃<br>                    |<br>                    CH₃ | |
| 16 | —C₄H₈N(CH₃)₂ | |
| 17 | —C₂H₄N⊕H₂CH₃ Cl⊖ | m.p. 105° |
| 18 | —C₂H₄N(CH₃)C₂H₅ | $n_D^{24}$ 1.5395 |
| 19 | 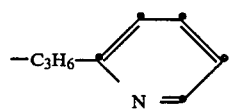 —C₃H₆— N | m.p. 72–75° |
| 20 | 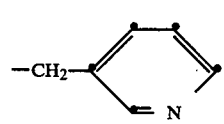 —CH₂— N | $n_D^{23}$ 1.5268 |
| 21 | —N=C(CH₃)₂ | m.p. 106–8° |
| 22 | 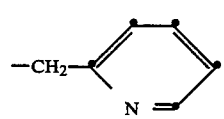 —CH₂— N | $n_D^{25}$ 1.5655 |
| 23 | 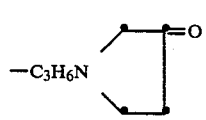 —C₃H₆N  =O | m.p. 95–98° |

-continued

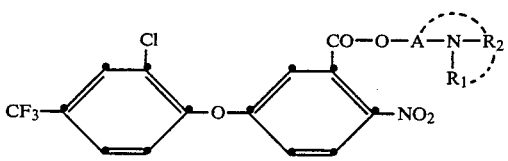

| No. | $\begin{smallmatrix}A-N-R_1\\|\\R_2\end{smallmatrix}$ | Physical constants |
|---|---|---|
| 24 | 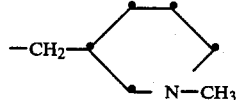 —CH₂—  N—CH₃ | $n_D^{23}$ 1.5460 |
| 25 | 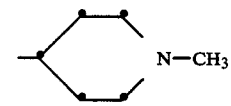  N—CH₃ | $n_D^{23}$ 1.5501 |
| 26 | —C₂H₄N⊕(CH₃)₃ I⊖ | m.p. 176–9° |
| 27 | 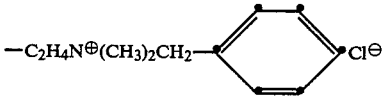 —C₂H₄N⊕(CH₃)₂CH₂— Cl⊖ | m.p. 143–6° |
| 28 | 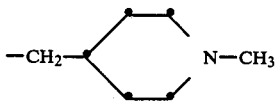 —CH₂—  N—CH₃ | |

Compositions according to the invention which contain as active ingredient at least one compound of the formula I are suitable in particular for selectively controlling wild grasses, which are difficult to control, in crops of cultivated plants, for example soya bean and cotton, by pre-emergence and especially post-emergence application.

The following test methods serve to verify the suitability of the said compositions as herbicides (pre- and post-emergence application).

Pre-emergence herbicidal action (inhibition of germination)

Immediately after sowing of the test plants in seed trays in a greenhouse, the surface of the oil is treated with an aqueous dispersion of the active substance, which has been prepared from a 25% emulsion concentrate, and from a 25% wettable powder containing active substances which cannot be produced as emulsion concentrates owing to inadequate solubility. Four different concentration series are used, corresponding to 4, 2, 1 and 0.5 kg of active substance per hectare. The seed trays are left in the greenhouse at 22°–25° C. with 50–70% relative humidity, and the test is evaluated after 3 weeks, the results being assessed according to the following scale of ratings:

1=plants have not germinated or have fully died off,
2–3=very strong action,
4–6=moderate action,
7–8=slight action, and
9=no action (as in the case of untreated control plants).

—=plant not tested at this concentration of active substance.

Post-emergence herbicidal action (contact herbicide)

In this test, the compound No. 1 has been compared with 2-nitro-5-(o-chloro-p-trifluoromethylphenoxy)-benzoic acid, known from U.S. Pat. No. 3,928,416, Example 48=compound A. The results are summarised in the Table which follows.

A largish number (at least 7) of weeds and of cultivated plants, both monocotyledonous and dicotyledonous, are sprayed after emergence (in the 4- to 6-leaf stage) with an aqueous active-substance dispersion in dosage amounts of 0.06, 0.125, 0.25, 0.5, 1, 2 and 4 kg of active substance per hectare, and they are then kept at 24°–26° C. with 45–60% relative humidity. The test is evaluated 15 days after treatment, and the results are assessed according to the same scale of ratings as that used in the pre-emergence test.

| Compound tested | No. 1 | | | | A | | | |
|---|---|---|---|---|---|---|---|---|
| Amount applied in kg/hect. | 4 | 2 | 1 | ½ | 4 | 2 | 1 | ½ |
| plant | | | | | | | | |
| soya bean | 8 | 8 | 9 | 9 | 3 | 4 | 5 | 5 |
| wheat | 3 | 7 | 8 | 9 | 2 | 4 | 4 | 8 |
| maize | 3 | 5 | 9 | 9 | 1 | 2 | 3 | 3 |
| abutilon sp. | 1 | 1 | 1 | 2 | 1 | 1 | 1 | 2 |
| sesbania exaltata | 1 | 1 | 1 | 2 | 1 | 1 | 1 | 1 |
| amaranthus retroflexus | 1 | 1 | 1 | 1 | 1 | 1 | 1 | 1 |
| ipomea purpurea | 1 | 1 | 1 | 2 | 1 | 1 | 1 | 1 |

The novel active substances of the formula I are stable compounds which are soluble in customary organic solvents, such as alcohols, ethers, ketones, dimethylformamide, dimethyl sulfoxide, and so forth.

The compositions according to the invention are produced in a manner known per se by the intimate mixing and grinding of active substances of the general formula I with suitable carriers and/or distributing agents, optionally with the addition of antifoaming agents, wetting agents, dispersing agents and/or solvents, all inert to the active substances. The active substances can be obtained and used in the following forms:
solid preparations: dusts, scattering agents, granules, (coated granules, impregnated granules and homogeneous granules);
water-dispersible concentrates of active substance: wettable powders, pastes, emulsions and emulsion concentrates; and
liquid preparations: solutions.

The concentration of active substance in the compositions according to the invention is 1 to 80 percent by weight, and when being applied to the compositions can if necessary contain the active substances also at a lower concentration, such as about 0.05 to 1 percent by weight.

Other biocidal active substances or compositions can be mixed with the described compositions according to the invention.

The following formulation examples are intended to further illustrate the production of solid and liquid preparations.

Emulsion concentrate

The following constituents are mixed together to produce a 25% emulsion concentrate:
25 parts of an active substance of the formula I,
5 parts of a mixture of nonylphenolpolyoxyethylene or calcium dodecylbenzene sulfate,
15 parts of cyclohexanone, and
55 parts of xylene.
This concentrate can be diluted with water to give emulsions of suitable concentration, for example 0.1 to 10%, and emulsions of this type are suitable for controlling weeds in crops of cultivated plants.

Granulate

The following substances are used to produce a 5% granulate:
5 parts of one of the active substances of the formula I,
0.25 part of epichlorohydrin,
0.25 part of cetyl polyglycol ether,
3.50 parts of polyethylene glycol, and
91 parts of kaolin (particle size: 0.3–0.8 mm).
The active substance is mixed with epichlorohydrin, and dissolved in 6 parts of acetone; polyethylene glycol and cetyl polyglycol ether are then added. The solution thus obtained is sprayed onto kaolin, and the acetone is subsequently evaporated off in vacuo.

Wettable powder

The following constituents are used to produce (a) a 70% wettable powder and (b) a 10% wettable powder:
(a)
70 parts of an active substance of the formula I,
5 parts of sodium dibutyl-naphthalene sulfonate,
3 parts of naphthalenesulfonic acid/phenolsulfonic acid/formaldehyde condensate (3:2:1),
10 parts of kaolin, and
12 parts of Champagne chalk; and
(b)
10 parts of an active substance of the formula I,
3 parts of a mixture of the sodium salts of saturated fatty alcohol sulfates,
5 parts of naphthalenesulfonic acid/formaldehyde condensate, and
82 parts of kaolin.
The given active substance is absorbed onto the appropriate carriers (kaolin and chalk), and the material is subsequently mixed and ground with the remaining constituents. Wettable powders having excellent wetting and suspension properties are obtained. It is possible to obtain from wettable powders of this type, by dilution with water, suspensions containing 0.1 to 80% of active substance, and these suspensions are suitable for controlling weeds in crops of cultivated plants.

Paste

The following substances are used to produce a 45% paste:
45 parts of an active substance of the formula I,
5 parts of sodium aluminium silicate,
14 parts of cetyl polyglycol ether having 8 mols of ethylene oxide,
1 part of oleyl polyglycol ether having 5 mols of ethylene oxide,
2 parts of spindle oil,
10 parts of polyethylene glycol, and
23 parts of water.
The active substance is intimately mixed and ground with the additives in apparatus suitable for the purpose. There is obtained a paste from which can be produced, by dilution with water, suspensions of any desired concentration.

What is claimed is:

1. A heterocyclic ester of 2-nitro-5-(o-chloro-p-trifluoromethylphenoxy)-benzoic acid of the formula

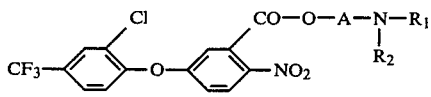

wherein

A is a branched-chain or straight-chain $C_2$–$C_4$ alkylene group, $R_1$ and $R_2$ taken together with the nitrogen atom to which they are attached or $R_1$ and a carbon atom of A taken together with the nitrogen atom to which $R_1$ is attached form a 3- to 7-membered heterocycle which optionally includes in its ring an oxygen atom, a sulfur atom or the group —$NR_3$— in which $R_3$ is hydrogen, $C_1$–$C_4$ alkyl, phenyl or benzyl, and $R_2$ when not forming part of the heterocyclic ring is a bond, hydrogen or $C_1$–$C_4$ alkyl, and acid addition or quaternary ammonium salts thereof.

2. An acid addition or quarternary ammonium salt of a compound according to claim 1.

3. A compound according to claim 1 which is 2-nitro-5-(o-chloro-p-trifluoromethylphenoxy)-benzoic acid-morpholinoprop-2'-yl ester.

4. The compound according to claim 1 which is 2-nitro-5-(o-chloro-p-trifluoromethylphenoxy)-benzoic acid-pyrid-2'-yl-methyl ester.

5. The compound according to claim 1 which is 2-nitro-5-(o-chloro-p-trifluoromethylphenoxy)-benzoic acid(3'-pyrid-2''-yl-propyl) ester.

6. The compound according to claim 1 which is 2-nitro-5-(o-chloro-p-trifluoromethylphenoxy)-benzoic acid (2'-pyrrolidino-ethyl) ester.

7. The compound according to claim 1 which is 2-nitro-5-(o-chloro-p-trifluoromethylphenoxy)-benzoic acid (pyrid-3'-ylmethyl) ester.

8. The compound according to claim 1 which is 2-nitro-5-(o-chloro-p-trifluoromethylphenoxy)-benzoic acid [3'-(3''-oxopyrrolidino)-propyl] ester.

9. The compound according to claim 1 which is 2-nitro-5-(o-chloro-p-trifluoromethylphenoxy)-benzoic acid (1'-methylpiperrid-3'-ylmethyl) ester.

* * * * *